United States Patent [19]
Lapeus et al.

[11] Patent Number: 5,674,047
[45] Date of Patent: Oct. 7, 1997

[54] LOADING MECHANISM FOR PROBE TIP TRAY

[75] Inventors: David J. Lapeus, Garfield Heights; James P. Polaniec, N. Ridgeville, both of Ohio

[73] Assignee: Chiron Diagnostics Corporation, East Walpole, Mass.

[21] Appl. No.: 501,855

[22] Filed: Jul. 13, 1995

[51] Int. Cl.⁶ .................................................. B65G 59/06
[52] U.S. Cl. ........................... 414/795.6; 414/797.4; 414/798.1
[58] Field of Search ........................... 414/795.6, 797.4, 414/797.8, 798, 798.1, 929

[56] References Cited

U.S. PATENT DOCUMENTS

| | | | |
|---|---|---|---|
| 3,298,565 | 1/1967 | Cease | 221/13 |
| 4,577,760 | 3/1986 | Rainin et al. | 206/508 |
| 4,599,026 | 7/1986 | Feiber et al. | 414/929 |
| 4,616,514 | 10/1986 | Magnussen, Jr. et al. | 73/864.14 |
| 4,676,377 | 6/1987 | Rainin et al. | 206/508 |
| 4,717,304 | 1/1988 | Bocchicchio et al. | 414/797.8 |
| 4,731,225 | 3/1988 | Wakatake | 422/65 |
| 4,748,859 | 6/1988 | Magnussen, Jr. et al. | 73/864.01 |
| 4,763,535 | 8/1988 | Rainin et al. | 73/864.18 |
| 4,770,588 | 9/1988 | Ripatonda | 414/795.6 |
| 4,905,526 | 3/1990 | Magnussen, Jr. et al. | 73/864.18 |
| 4,971,514 | 11/1990 | Hunter | 414/795.3 |
| 4,991,741 | 2/1991 | Anderson | 221/223 |
| 5,055,262 | 10/1991 | Sakagami | 422/64 |
| 5,128,105 | 7/1992 | Berthold et al. | 422/104 |
| 5,392,914 | 2/1995 | Lemieux et al. | 206/499 |
| 5,480,280 | 1/1996 | Bordon | 414/798.1 |

FOREIGN PATENT DOCUMENTS

| | | | |
|---|---|---|---|
| 0301583 | 2/1989 | European Pat. Off. | G01N 35/02 |
| 4436473 | 3/1996 | Germany | B01L 9/06 |
| 2224498 | 5/1990 | United Kingdom | 414/798.1 |

*Primary Examiner*—William E. Terrell
*Assistant Examiner*—Gregory A. Morse
*Attorney, Agent, or Firm*—Charles Gagnebin, III; Judith A. Roesler; Robert P. Blackburn

[57] ABSTRACT

In a system for installing, from a supply of disposable probe tips, one such probe tip on a probe for each sample by an automated fluid analyzer system and for removing the tip after each use to allow a fresh tip to be installed, a mechanism for making a fresh supply of tips available in a carrier tray and for receiving and disposing of empty carrier trays. Multiple probe tip trays, each having a base, a lid, and holding an array of tips are stacked within a chute of the mechanism. A pair of arms are swung up from a substantially vertical position to a horizontal position beneath the chute. An associated latch engages the lid of the lowermost tray within the chute while tray guides, which hold the trays within the chute, separate to release the lowermost tray onto the pair of arms. A delivery rack associated with the analyzer system receives the lowermost tray base from the pair of arms by engaging the tray base with a pair of clips. The rack then removes the base, and the probes thereon, to the analyzer system. The pair of arms meanwhile lower and dump the lid into a waste receptacle or disposal chute. The delivery rack thereafter returns an empty base to the parallel arms, which similarly dump empty base into the waste receptacle or disposal chute. The cycle is repeated by removing the next tray from the chute.

27 Claims, 16 Drawing Sheets

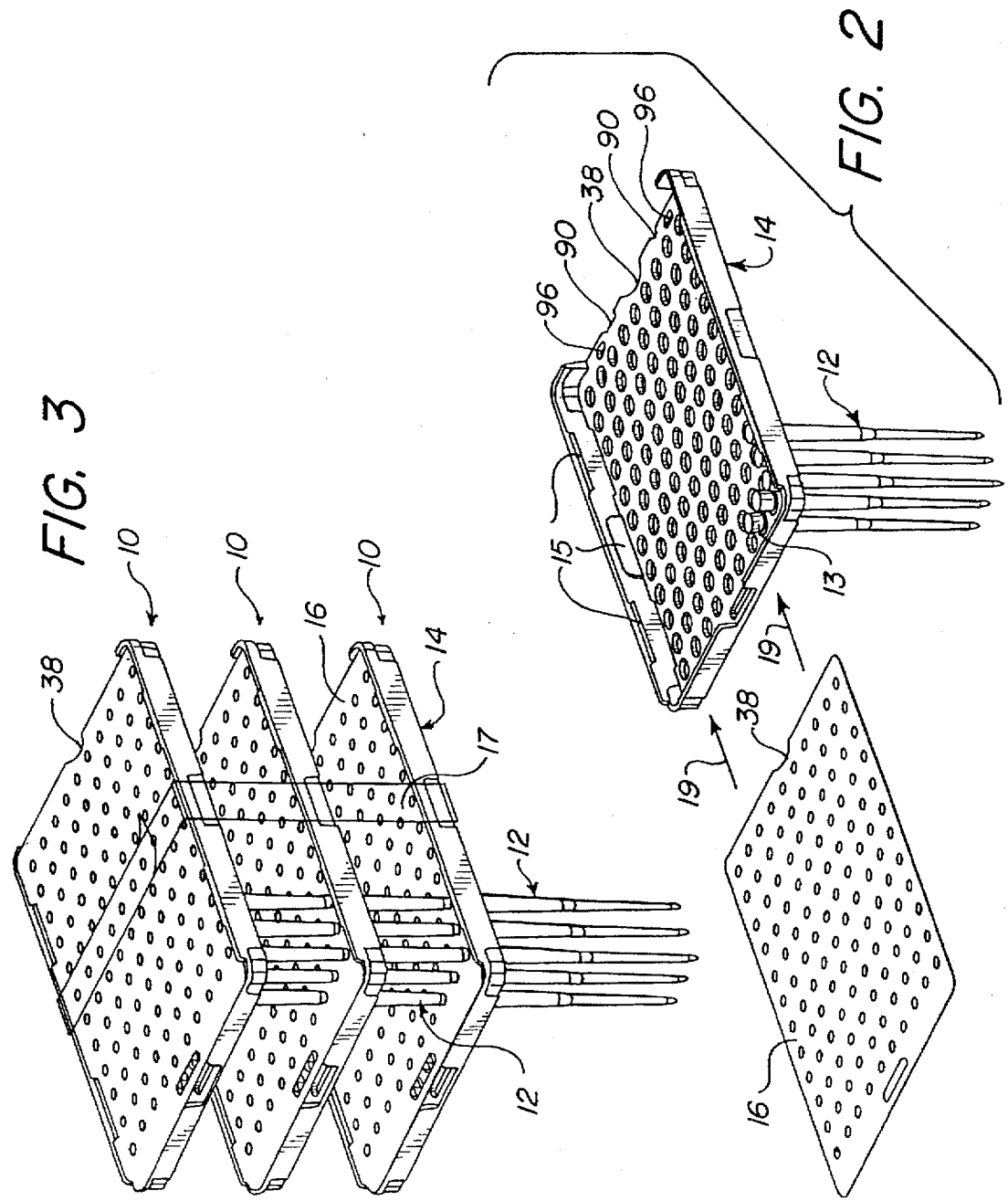

FIG. 9
FIG. 10

LOADING MECHANISM FOR PROBE TIP TRAY

FIELD OF THE INVENTION

The present invention relates to the field of piece part loading mechanisms, and in particular to a loading mechanism for transferring trays of disposable probe tips.

BACKGROUND OF THE INVENTION

As is known in the art, there is a trend in hospitals, clinics, laboratories and other locations to perform tests (assays) on samples of patient specimens such as blood, spinal fluid, urine, serum, plasma, and the like using automated analyzer systems. Relatively sophisticated automated analyzer systems typically accept a plurality of different patient specimen samples and perform different tests on each of the different samples.

One sample in such systems must not be allowed to contaminate another sample. Devices such as aspirating probes may use disposable probe tips with each sample to avoid such contamination. Therefore, one problem which arises involves the automated provision of a large quantity of disposable probe tips or like elements. Such provision typically involves frequent intervention by technicians who must have some familiarity with replenishment of such disposable elements.

In keeping with the intended functionality of automated analyzer systems, such tip provision should involve minimal human intervention. Further, any required human intervention should be as intuitive and fool-proof as possible.

It would, therefore, be desirable to provide a mechanism for supplying an uninterruptable quantity of disposable elements such as probe tips for dispensing said quantity to an automated analyzer system as required.

SUMMARY OF THE INVENTION

The present invention provides a mechanism for providing a plurality of disposable probe tips to a system such as an automated analyzer system. Multiple trays of probe tips are loaded into a chute of the mechanism. A pair of arms, riding atop a vertical shaft, are swung up from a substantially vertical position to a horizontal position as the shaft is elevated beneath the chute. As the shaft reaches its upper travel limit, a leaf spring and associated latch are urged away from a lowermost tray in the chute. Simultaneously, tray guides, which hold the trays within the chute, are rotated away from the trays in preparation for releasing the lowermost tray. At the shaft upper travel limit, the leaf spring and latch snap over the upper surface of the lowermost tray, engaging a tray lid, while the tray guides separate, releasing the lowermost tray onto the pair of arms.

A delivery rack, associated with a proximate analyzer system, proceeds beneath the parallel arms, and receives the tray by engaging a tray base portion with a pair of clips. The delivery rack then removes the base portion, and the probe tips disposed thereon, to the analyzer system. Meanwhile, the shaft lowers, causing the parallel arms to relax into the vertical position, thus dumping the lid into a waste receptacle or disposal chute.

When the analyzer system has consumed the probe tips disposed in the tray base portion, the delivery rack returns the base portion to the parallel arms, which then dumps the empty base portion into the waste receptacle or disposal chute. The cycle then begins anew.

It is an object of the present invention to provide a microprocessor-based control unit to enable provision of an endless quantity of probe tips disposed in trays, limiting the required interaction of technicians or support personnel to occasional restocking of the mechanism. It is a further object to make such hands-off provision as simple and intuitive as possible by providing features which prevent incorrect tray loading into the chute. Sensors are provided in alternative embodiments to sense an empty chute condition and to sense bundled trays, thus addressing the further object of providing an intelligent probe tip provision system.

BRIEF DESCRIPTION OF THE DRAWINGS

These and other features of the present invention are more fully set forth below in the fully exemplary detailed description and accompanying drawings of which:

FIG. 2 is a partially exploded view of a probe tip tray as used in the loading mechanism of FIG. 1;

FIG. 3 is a perspective view of a pack of trays for use in the loading mechanism of FIG. 1;

FIG. 9 is a right side view of the tray base portion of FIG. 4;

FIG. 10 is a left side view of the tray base portion of FIG. 4;

DETAILED DESCRIPTION

Figure 1:
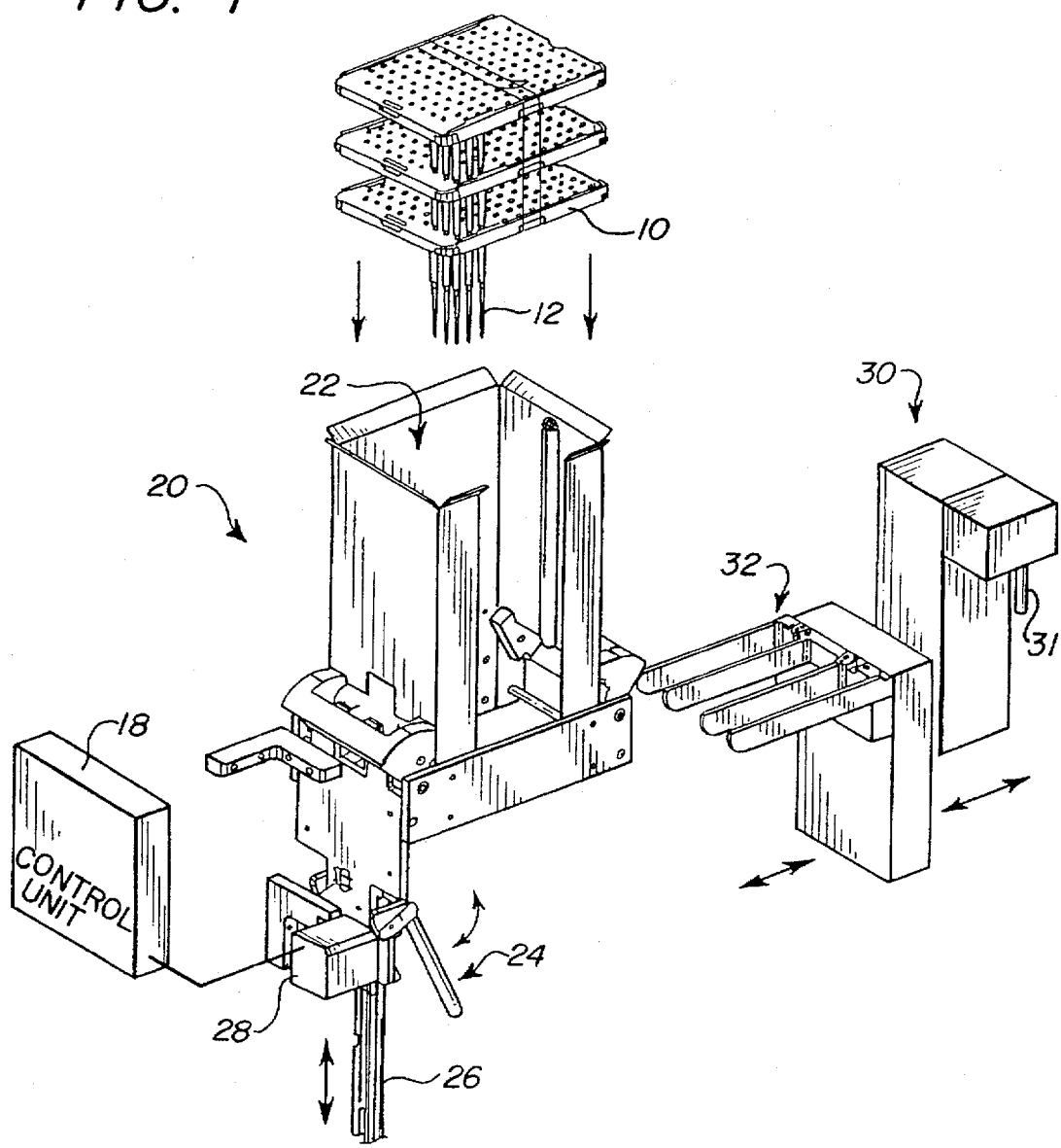
FIG. 1 is a partially exploded view of elements of the loading mechanism of the present invention.
Figure 4:
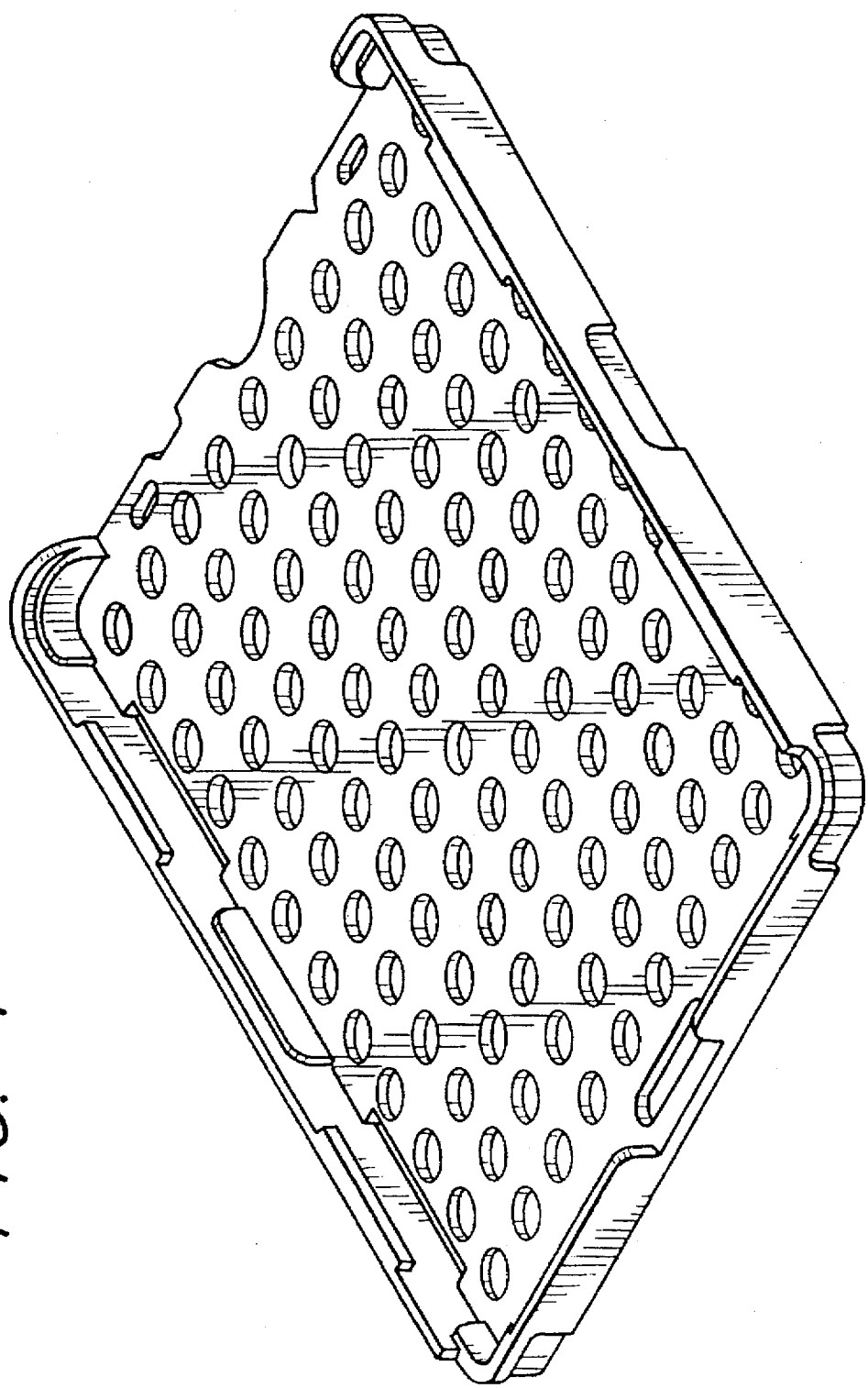
FIG. 4 is a top-right-front perspective view of a tray base portion as used in the loading mechanism of FIG. 1.
Figure 5:
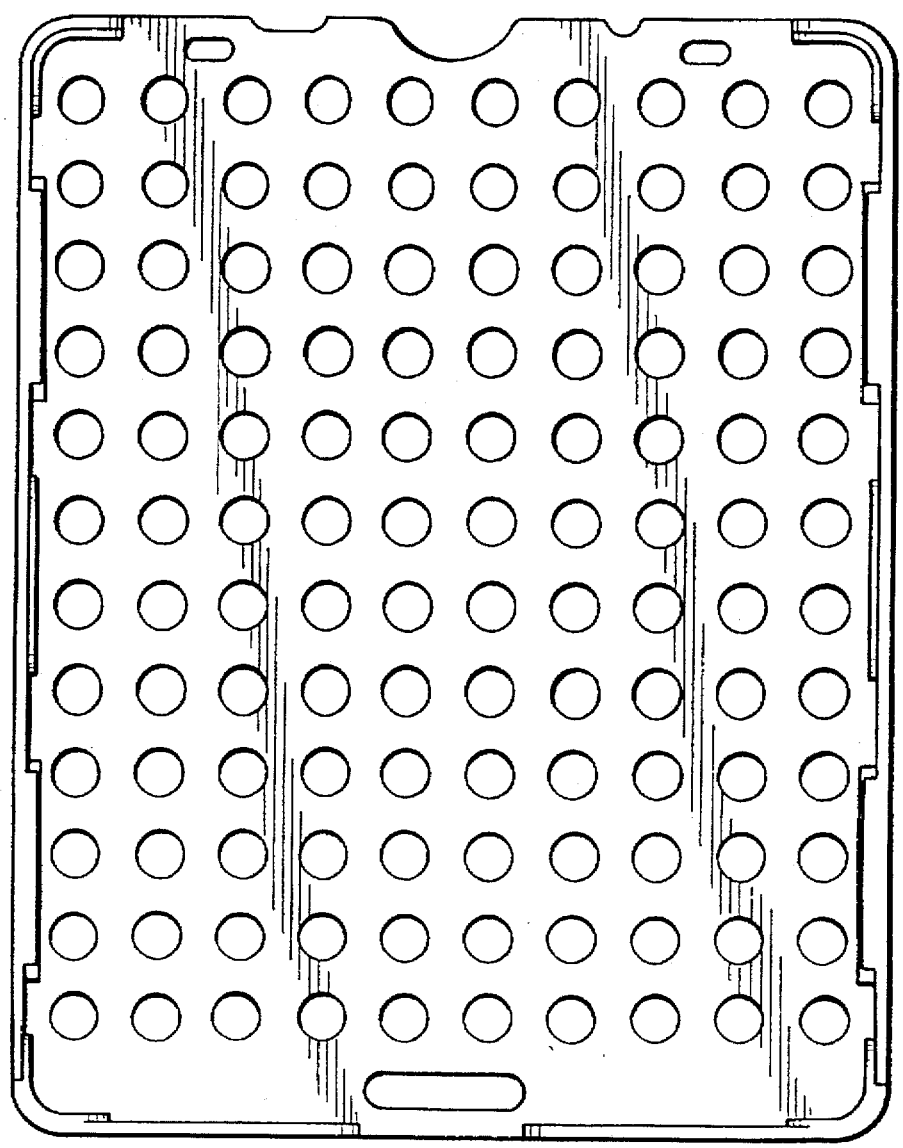
FIG. 5 is a top view of the tray base portion of FIG. 4.
Figure 6:
FIG. 6 is a front view of the tray base portion of FIG. 4.
Figures 7, 8:
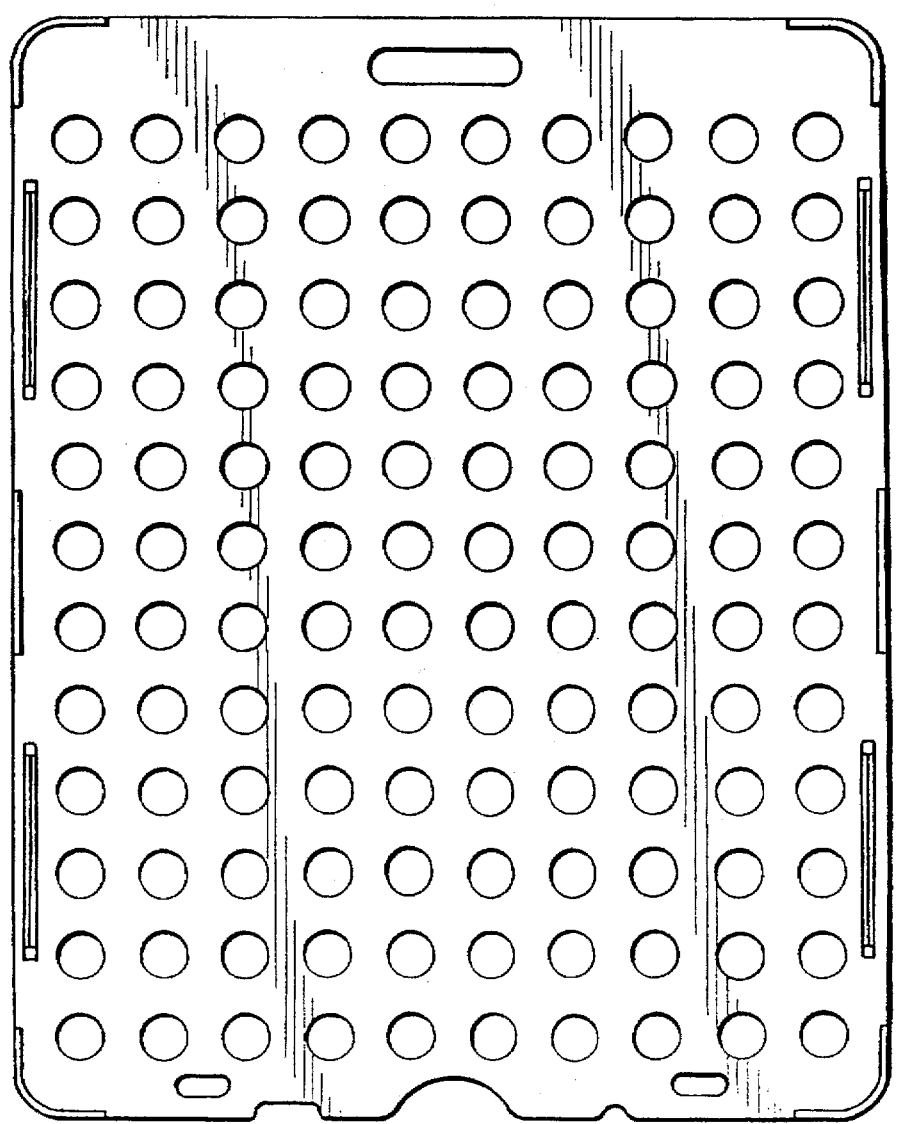
FIG. 7 is a rear view of the tray base portion of FIG. 4.
FIG. 8 is a bottom view of the tray base portion of FIG. 4.

An overview of a first embodiment of the present invention is provided in FIG. 1. In general, the present invention enables a user to load multiple trays 10, each supporting a plurality of disposable probe tips 12, into a chute 22 of a loading mechanism 20. In the illustrated embodiment, up to six such trays 10 can be loaded into the chute 22 at once. As will be illustrated in further detail subsequently, the probes from a first tray nestle into interior regions of corresponding probes in a second, underlying tray, thus reducing vertical space requirements.

In general, when a tray 10 of probes is required by an automated analyzer system, generally referred to as 30, a pair of parallel arms 24 is brought beneath the chute and conveys the lowermost tray 10 onto a delivery rack 32 which moves horizontally with respect to both the loading mechanism 20 and the analyzer system 30. This rack 32, driven by a motor, for example, then transports the tray 10 to the analyzer system 30, which in one embodiment includes a probe 31 requiring disposable probe tips. Once the delivery rack 32 is in position proximate the analyzer system 30, the probe 31 is manipulated in two-dimensions to mount and remove the next available disposable tip 12 from the tray 10. A motor 28 provides the power for raising and lowering a shaft 26 on which the arms 24 are mounted. In a first embodiment of the present invention, the motor 28 and delivery rack 32 respond to controls from a microprocessor-based control unit 18.

After all of the probe tips from the tray 10 have been consumed within the analyzer system 30, the delivery rack 32 returns the tray 10 to the parallel arms 24 for disposal, and the cycle can begin again.

With reference to FIGS. 2 and 3, the trays 10 and associated probe tips 12 are described. Each tray 10 is formed of a base portion 14 and a tray lid 16. The base portion 14 is provided with a plurality of holes, preferably disposed in a two-dimensionally aligned pattern, through which the probe tips 12 are disposed. Upper collars 13 of each probe tip are of a diameter larger than the holes, thus preventing the tips 12 from falling through the holes in the base 14. One-hundred twenty probe tips are provided in each illustrated tray 10, the latter being injection molded plastic in one embodiment. Further, the tray bases 14 and lids 16 are recyclable in a preferred embodiment.

In order to prevent the loaded tips 12 from being pushed up and out of the tray base 14, a lid 16 is provided having holes corresponding to the holes in the tray base 14 and of a diameter smaller than the diameter of the probe tip upper collars 13. Thus, upward force on the probe tips 12 is resisted by the overlying lid 16. The lid 16 mates with the tray base 14 in a first embodiment by sliding horizontally (in the direction of arrows 19) on guides 15 disposed within the base 14.

The lid 16 holes are aligned with the holes in the tray 14 to facilitate stacking of multiple trays 10. Specifically, a portion of the probe tips 12 extending from an upper tray 10 are inserted into the interior of corresponding probe tips 12 disposed in an underlying tray 10. Features provided on the exterior of each probe tip 12 limit the insertion distance. In one embodiment, packs of three probe tip trays 10 are provided, held together with a packaging band 17. After insertion of the trays 10 within the loading mechanism 20, as illustrated in FIG. 1, it is important to remove this band 17, since only one tray 10 at a time is provided to the analyzer system 30. In a further embodiment of the presently disclosed invention, a sensor is provided in the chute 22 to determine if the band 17 is present. If it is, the user is notified of this condition, and the mechanism will not attempt to load a tray until the band 17 has been removed.

Detailed views of a first tray base portion 14 embodiment are provided in FIGS. 4 through 10.

Figure 11:
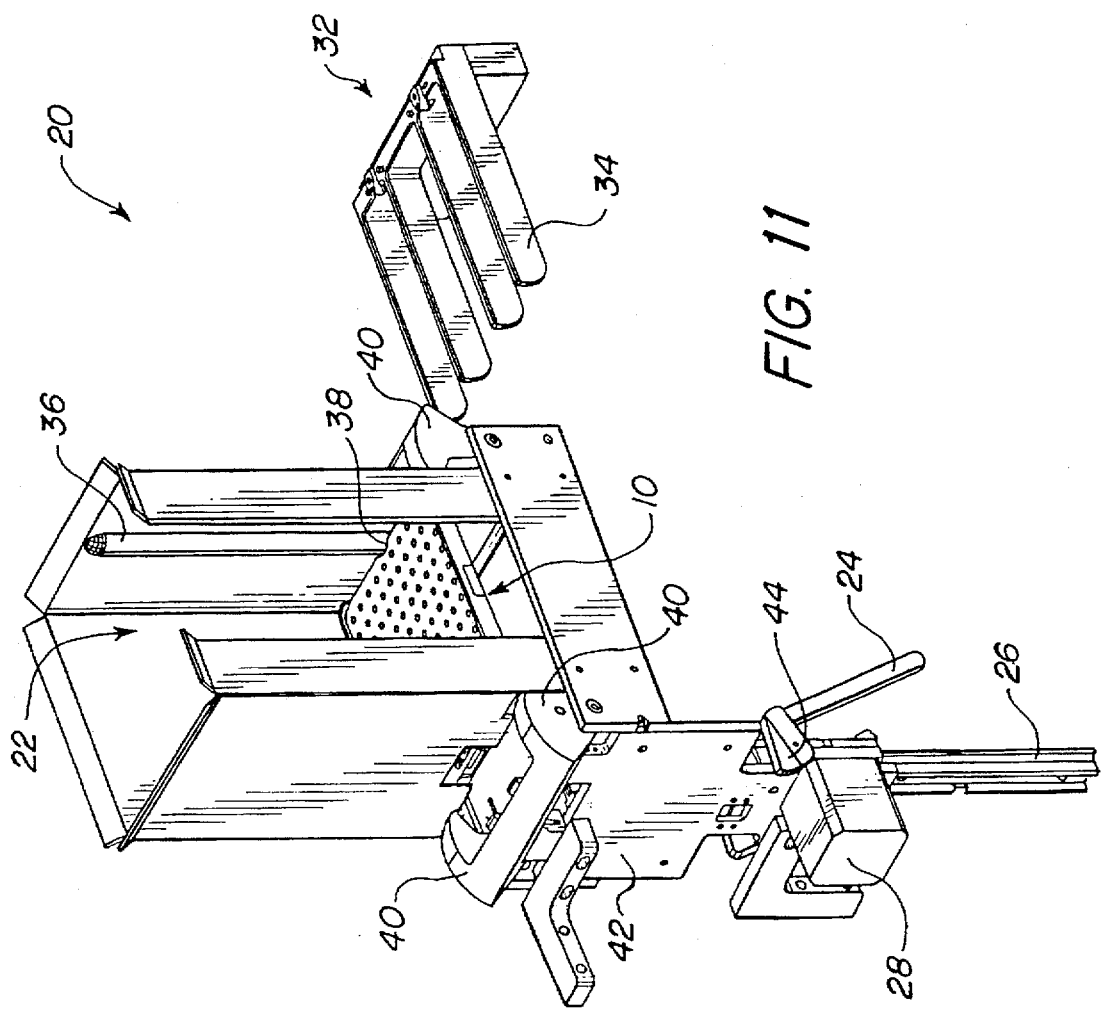
FIGS. 11, 12 and 13 illustrate relative positions of the loading mechanism elements of FIG. 1 in the initial stages of transferring a tray.

The operation of the loading mechanism 20 is now described with reference to FIGS. 11 et seq. In these illustrations, the analyzer system 30 is not illustrated to avoid excess distraction from the present invention. Also in FIGS. 11 et seq., only one tray 10 is illustrated, and this without probe tips 12, again for reasons of simplicity. Similarly, various support plates and structural members are omitted in order to provide better views of the function of the loading mechanism 20.

As noted, up to six trays can be installed in the chute 22 of the illustrated embodiment, and a larger or smaller number is possible in other embodiments. Once installed in the chute 22, probe tips 12 hanging from the lowermost tray 10 extend below the chute 22. For the purposes of discussion, the movement of only one tray 10 within the present mechanism is described, this being the lowermost tray 10 in the chute 22.

Proper installation of the tray 10 within the chute 22 is ensured by provision of a vertically aligned protrusion 36 on one wall of the chute 22, the tray 10, including the base 14 and lid 16 portions, having a cooperating notch 38 on one edge. Within the chute 22, the installed tray 10 rests upon opposing pairs of tray guides 40 which temporarily prevent the tray 10 from falling from the chute. For the purposes of illustration, it is assumed that no tray base portions 14 have been installed in the present system, and therefore it is not necessary to clear the automated analyzer system 30 of an empty tray base 14, though the processing of this situation will be discussed subsequently.

The transfer of a full tray 10 to the analyzer system 30 begins, after loading the chute 22 with at least one tray 10, by elevating a pair of parallel arms 24 pivotably disposed on a vertical shaft 26. This shaft 26 in a preferred embodiment has vertically aligned horizontal teeth along one surface forming a rack 25, as shown in the shaft cross-sectional view of FIG. 15. The rack 25 is provided as a separately mounted element in a first embodiment. A proximate motor 28 has a cog on a drive shaft (not shown in FIGS. 11 or 15), the cog acting as a pinion. This motor 28 is mounted on a first plate 42 extending below the chute 22. Other L-shaped elements or gussets disposed upon this first plate 42 are used for mounting the present mechanism onto a portion of the analyzer system 30 or some other support structure.

Figure 12:
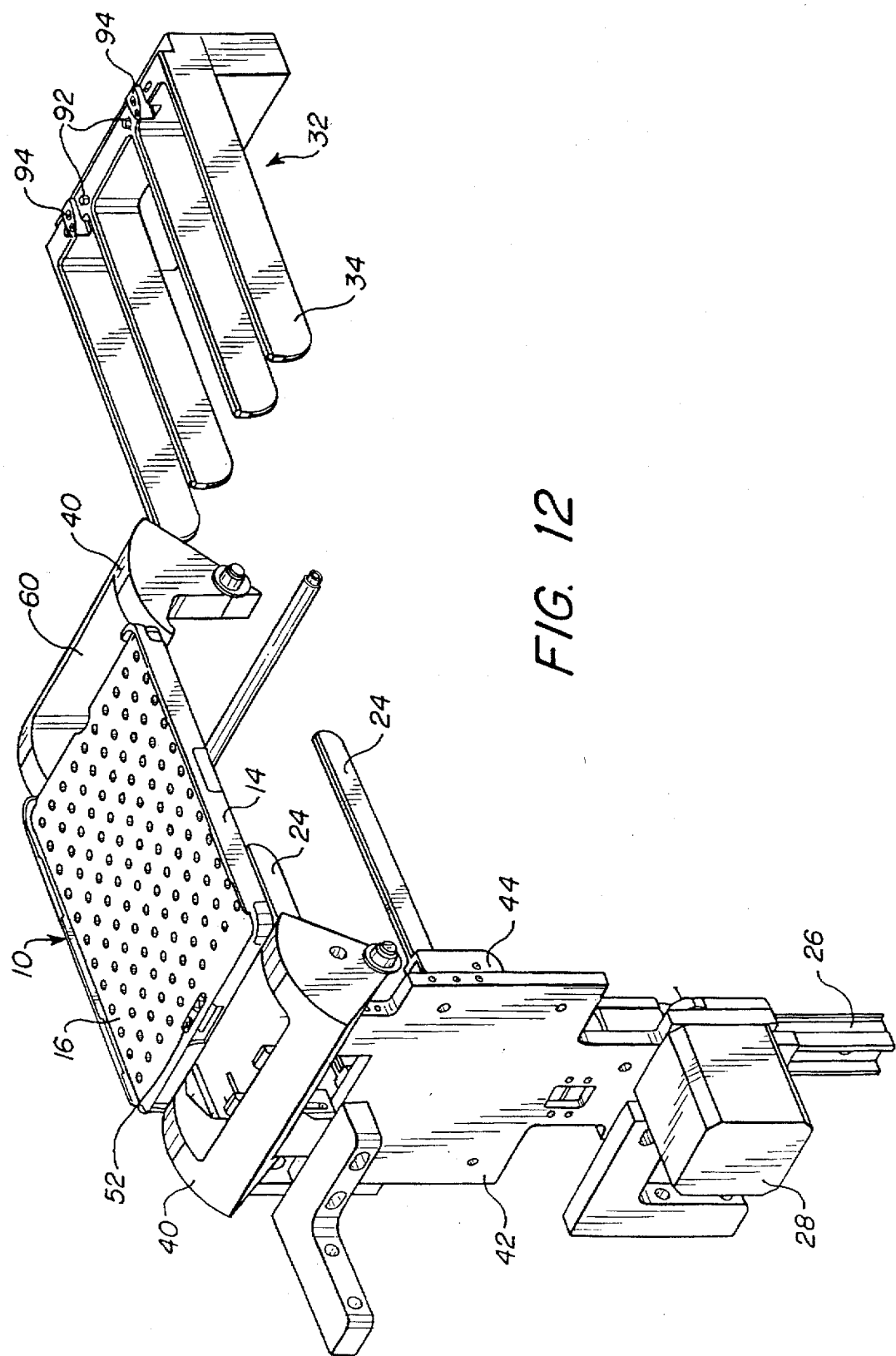

The parallel arms 24 rotate about a horizontal pivot 54 disposed atop the shaft 26. The parallel arms 24 terminate at the horizontal pivot 54 in cams 44, and in a first position point generally downward (FIG. 11). As the arms 24 are elevated by the shaft 26, the cams 44 come into contact with the first plate 42, and the arms 24 are forced into a horizontal second position under the chute 22 (FIG. 12). As shown in FIG. 12, wherein the chute 22 has been omitted for purposes of illustration, the tray 10 remains on the tray guides 40 as the arms 24 are raised toward the second position, though the tray 10 is released when the arms 24 reach the second position, as described subsequently.

Figure 13:
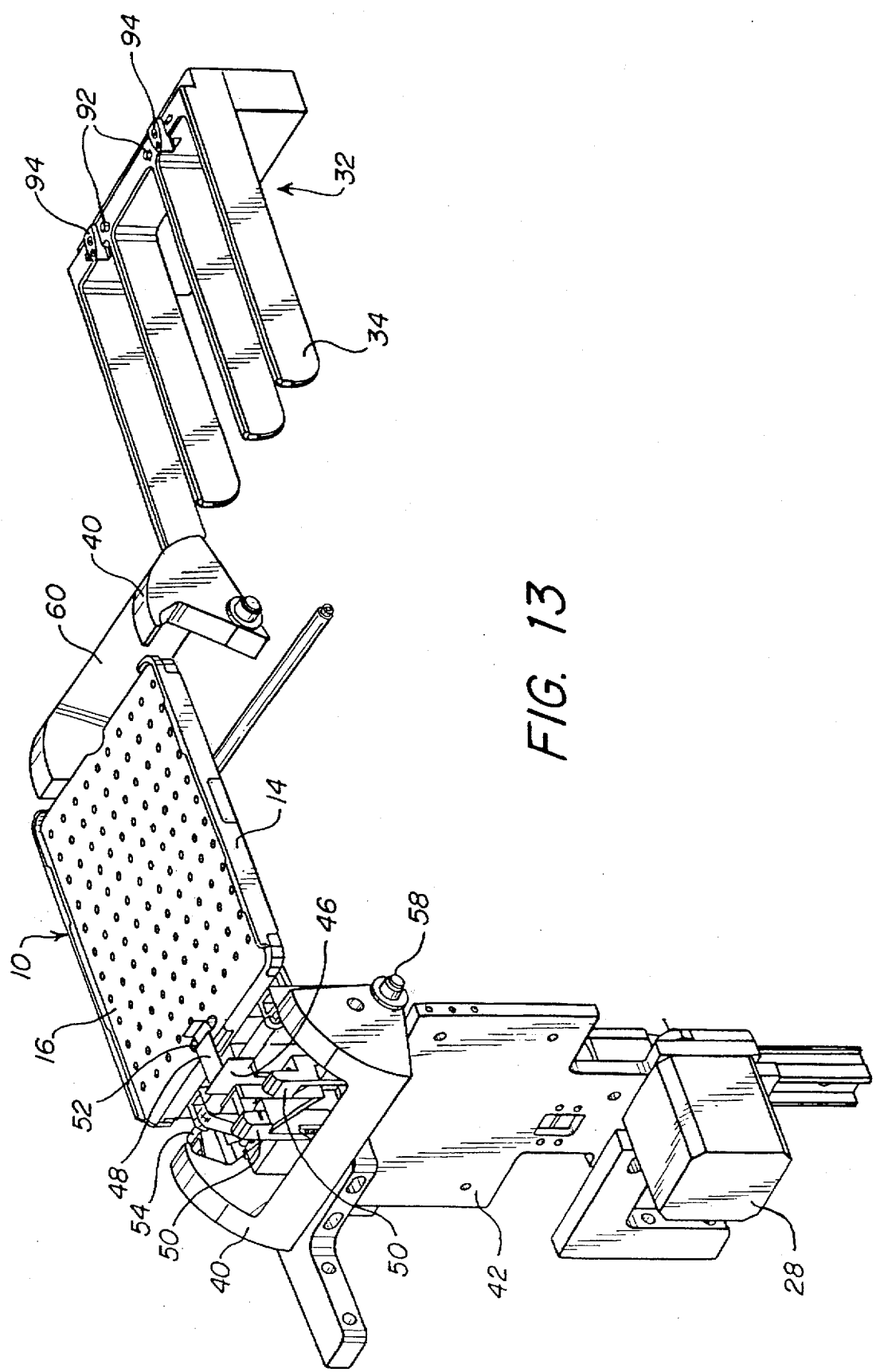
Figure 14:
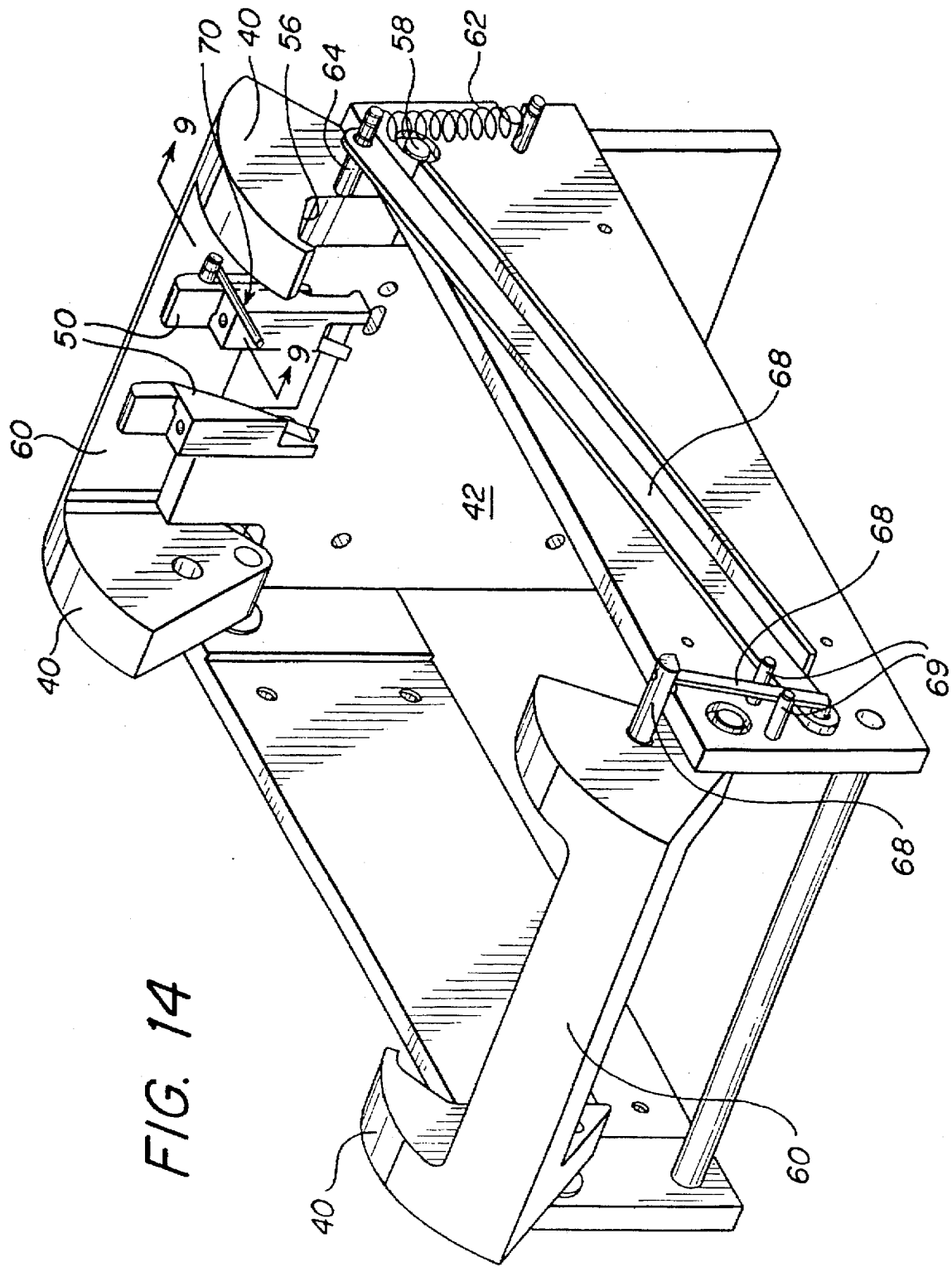
FIG. 14 is a reverse angle perspective view of loading mechanism elements of FIG. 1.

With reference to FIGS. 13 and 14, further elevation of the shaft 26 and associated arms 24 forces a leaf spring 46 disposed at an upper end of the shaft 26 to slide outward along angled surfaces of two spring guides 50. A latch 48 disposed at a right angle to the leaf spring is thus moved away from the tray as it is elevated at the upper end of the shaft 26. At the upper travel limit of the shaft 26, the spring guides terminate, allowing the leaf spring 46 to snap back towards the lowermost tray 10 installed in the chute 22. The leaf spring latch 48 is thus positioned adjacent the lid 16 and into an aperture 52 formed therein.

Figure 15:
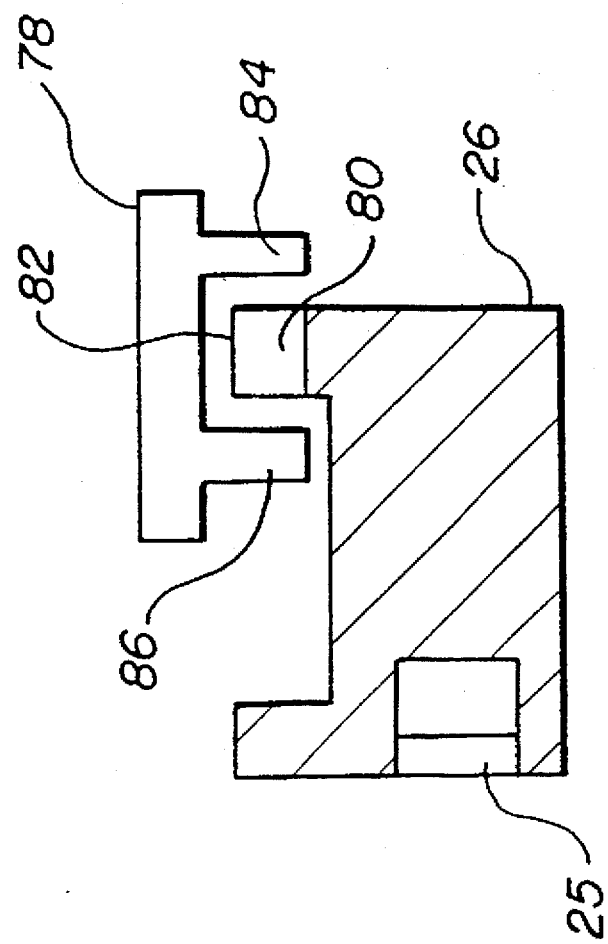
FIG. 15 is a top section view of a shaft and associated slotted optical sensor for use in the loading mechanism of FIG. 1.

The upper travel limit of the shaft 26, and other critical positions, are determined in one embodiment by the use of a slotted optical sensor 78 in association with the shaft 26, as shown in FIG. 15. A slot 80 is cut out of a vertical rail 82 on the shaft 26 at a position intermediate a source 84 and a detector 86 of the optical sensor 78 when the parallel arms 24 are in a desired position. When the shaft 26 is oriented so that light energy passes from the source 84 to the detector 86, the sensor 78 provides a position signal to the control unit 18, which in turn uses this positional information to control the motor 28. Multiple slots 80 can be provided in the shaft 26, depending upon the embodiment. One slot 80 can be used for each critical shaft 26 position. Alternately, a limited number of slots can be provided, with the control unit 18 commanding the motor 28 to raise or lower the shaft 26 a known distance from a slot position to orient the arms 24 in another position.

Simultaneous to the manipulation of the leaf spring 46 upon elevation of the shaft 26, the shaft horizontal pivot 54 progresses against an inner surface 56 one of the tray guides 40, forcing that tray guide 40 to rotate about a tray guide axis 58 and away from the tray 10 disposed thereon. Each pair of tray guides 40 is joined by an interconnecting member 60, so that rotation of one tray guide 40 due to horizontal pivot 54 pressure on an inner surface 56 causes simultaneous rotation of the other tray guide 40 linked by the interconnecting member 60. The tray guides 40 proximate the shaft 26 are urged in either an inward position (FIG. 14) or an outward position (FIG. 13) by an over-center spring 62. The limit pins 69 provide mechanical stops for the tray guides 40.

In order to bring about coordinated movement in an opposite pair of tray guides 40, the pair closest to the shaft 26 provide a rod 64 and linkage 68 to the distal pair. Thus, as the closest pair of tray guides 40 transition from a position supporting a tray 10 within the chute 22 to an outward position allowing the lowermost tray 10 to pass out of the chute 22, the distal pair of tray guides 40 move in unison.

Figure 16:
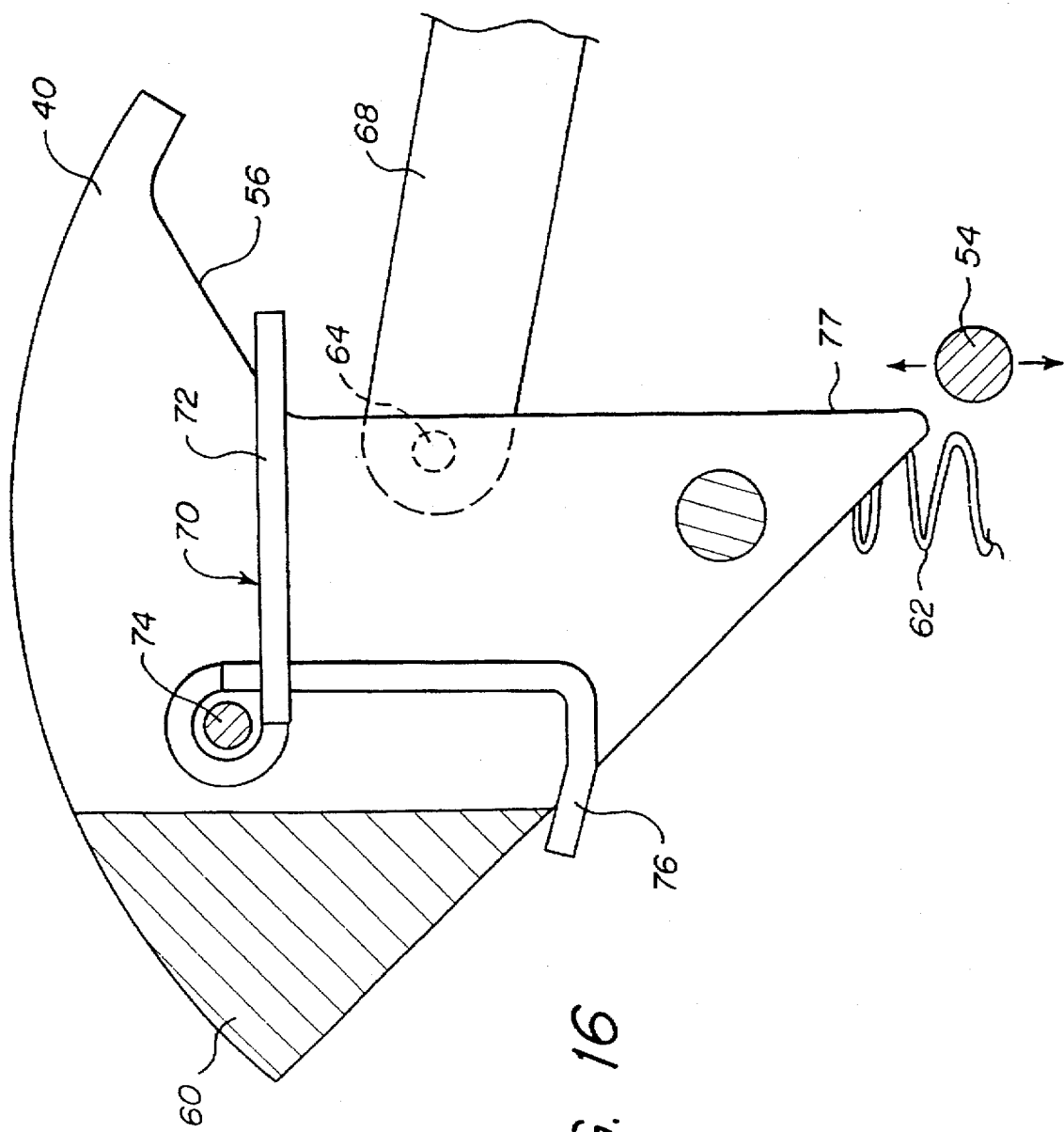
FIG. 16 is a side section view of a tray guide and tray guide locking feature for use in the loading mechanism of FIG. 1.

In order to prevent inadvertent outward rotation of the linked tray guides 40, potentially resulting in the accidental dumping of loaded trays 10, the tray guides 40 and interconnecting member 60 closest to the shaft 26 are provided with a locking feature 70, explained with respect to FIG. 16. This view illustrates a portion of the tray guide interconnecting member 60, the tray guide 40 proximate the over-center spring 62, the spring 62, the tray guide rod 64 (in phantom), a portion of the tray guide linkage 68, and the location of the tray guide locking feature 70 with respect to these elements.

The tray guide 40 and interconnecting member 60 are shown in an inward, locked position. In other words, the shaft 26 has not risen to its upper travel limits yet. The elevation of the pivot shaft 54 also has the effect of rotating a locking feature horizontal end 72 upwards, or counter-clockwise in FIG. 16. This causes the feature 70 to rotate counter-clockwise about a pin 74, and withdraws a hooked portion 76 from beneath a lower edge of the tray guide interconnecting portion 60. Without this action, the hooked portion interferes with the free rotation of the locking feature 70, thus preventing the tray guides 40 from rotating outwardly.

Lowering the shaft 26 from the elevated position causes the shaft horizontal pivot 54 to strike a lower surface 56 of the outwardly angled tray guide 40 most proximate the over-center spring 62, thus rotating the tray guides 40 from the outward position to the inward position. The locking feature 70 does not interfere with this inward rotation. Thus, the tray guides 40 are prevented from releasing a tray 10 unless the shaft 26 and associated parallel arms 24 are in position for receiving the lowermost tray. Once this tray is received and lowered away from the chute 22 (as next described), the tray guides 40 are returned to the inward position.

Figure 17:
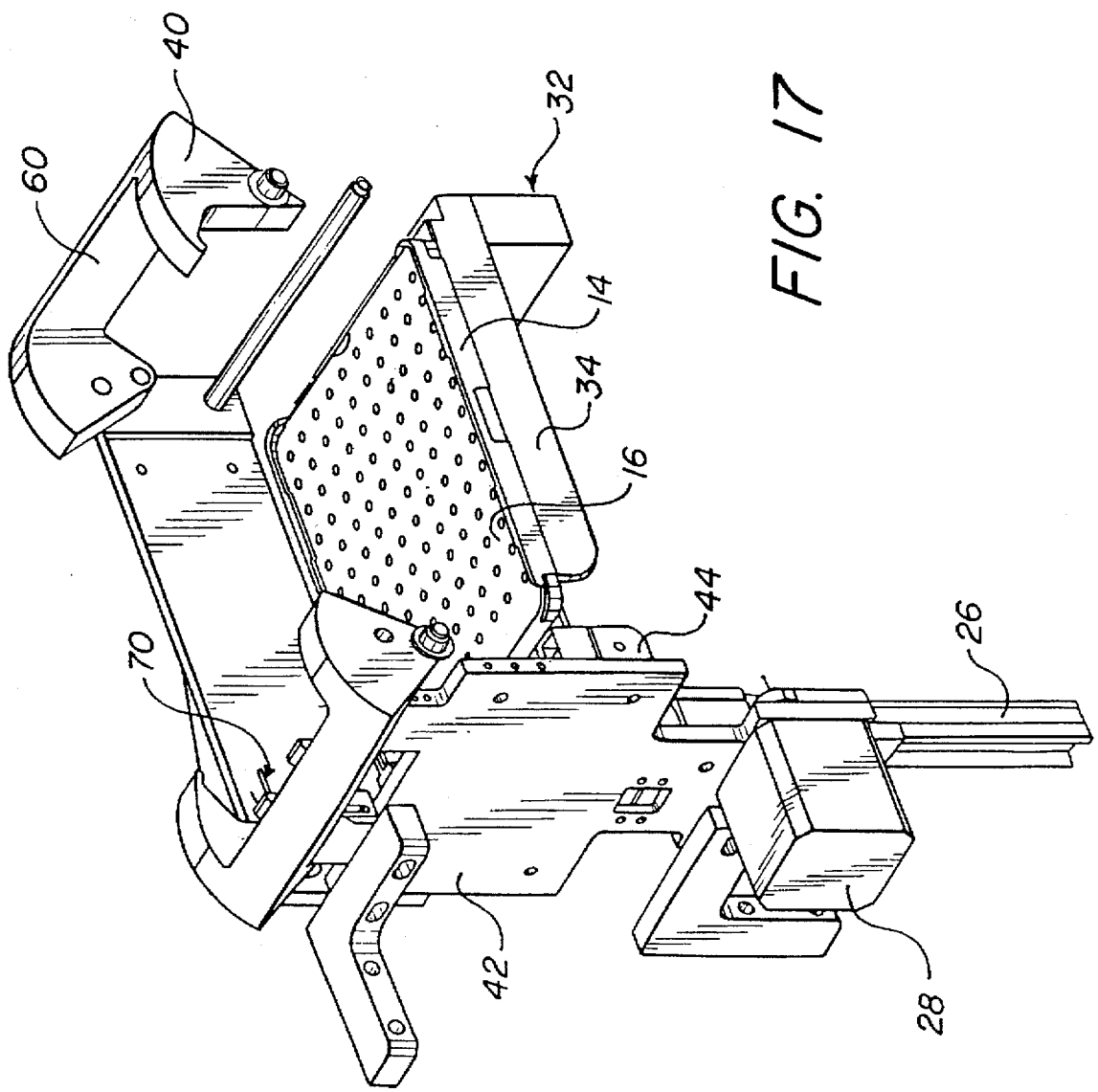
FIGS. 17, 18 and 19 illustrate relative positions of the loading mechanism elements of FIG. 1 in further stages of transferring a tray.

With regard to FIG. 17, the process of lowering the tray 10 away from the chute 22 is now described. The released tray 10 rests upon the parallel arms 24, and is retained by the leaf spring latch 48 disposed in the lid aperture 52. The delivery rack 32 is driven horizontally to a position substantially, but not completely, under the parallel arms 24 in preparation for receiving the released tray 10.

The shaft 26 is lowered and the released tray 10 is deposited onto the delivery rack fingers 34. The delivery rack 32 is then further driven under the tray 10. One or more notches 90 (FIG. 2) on the released tray 10 align with a cooperative post or posts 92 (FIG. 12) extending from the delivery rack 32 to ensure proper alignment.

Figure 18:
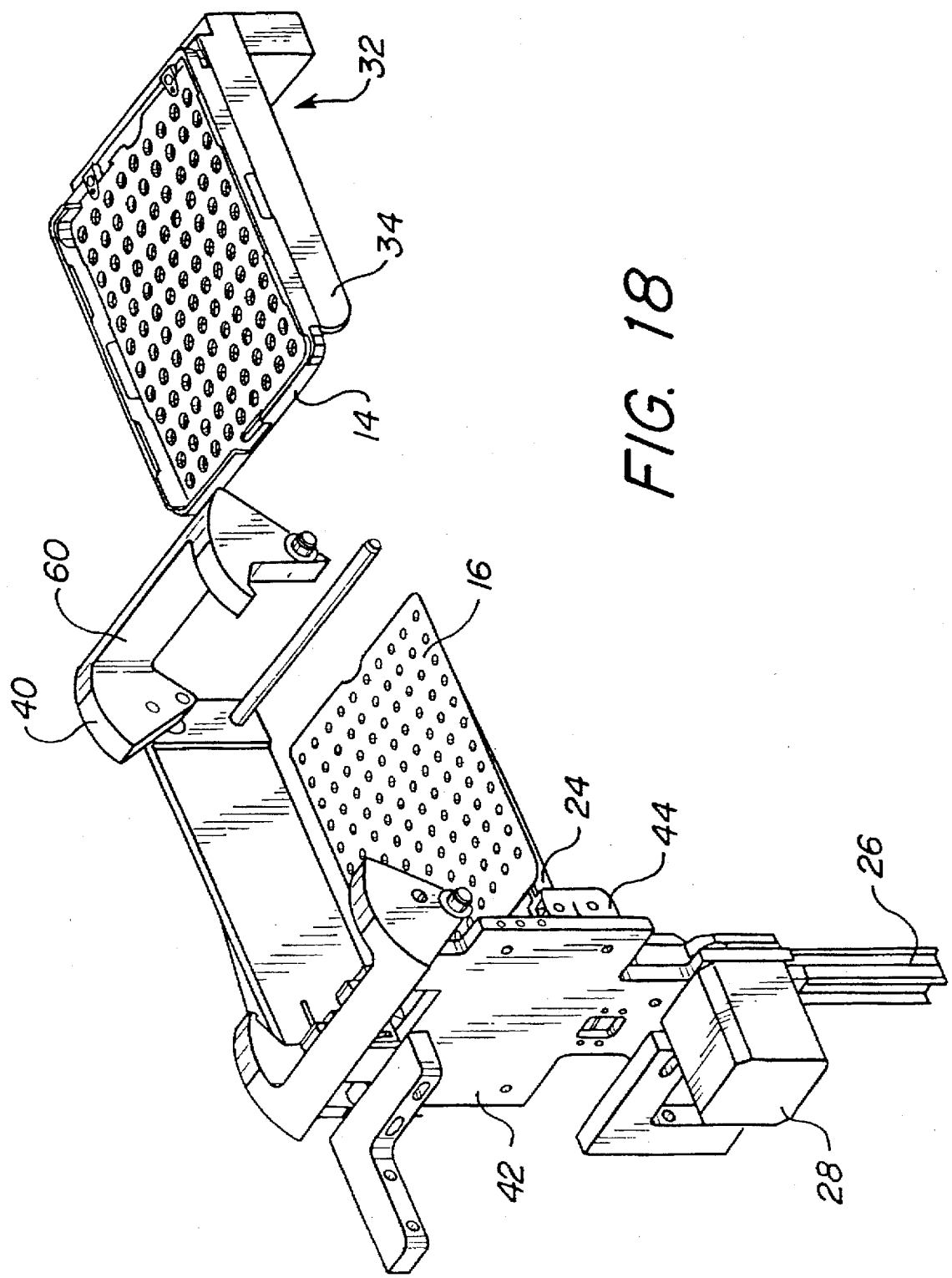

With reference to FIGS. 2 and 18, the delivery rack further provides one or more clips 94 which grip the tray base portion 14 at cooperating apertures or features 96 formed in the tray base portion 14. These clips 94 enable the delivery rack 32 to withdraw the tray base portion 14, with its compliment of probe tips away from the lid 16 which initially remains in the grasp of the leaf spring latch 48 associated with the shaft 26.

Figure 19:
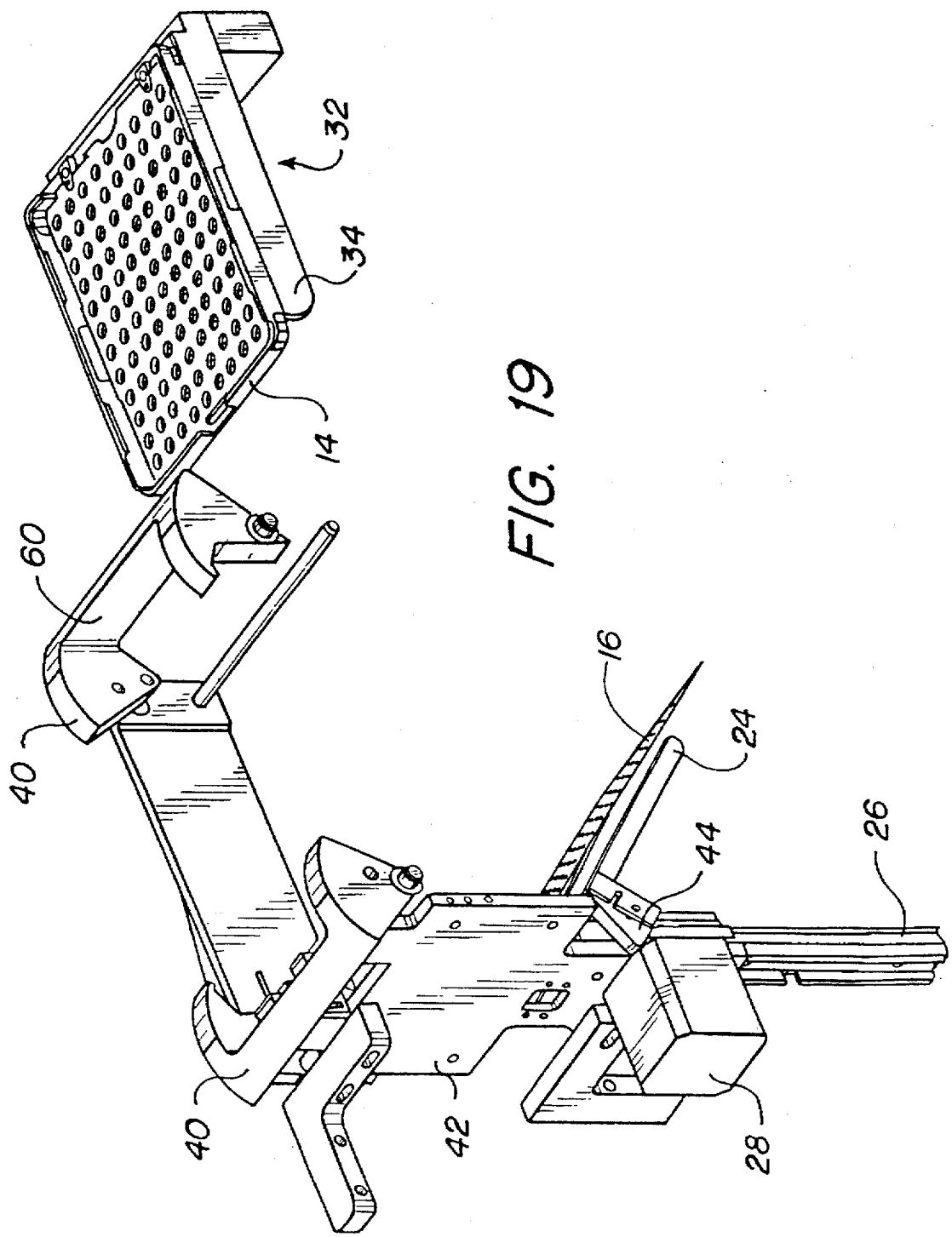

Once the tray base portion 14 has been fully removed by the delivery rack 34, the lid portion 16 falls from the leaf spring latch 48 and onto the parallel arms 24 by force of gravity. The lid 16 is no longer required, and is dumped from the parallel arms 24 by lowering the shaft 26 until the cams 44 disengage from the first plate 42 and the arms 24 angle downward, as shown in FIG. 19. In one embodiment, a disposal chute or receptacle (not illustrated) is positioned below the illustrated mechanism for receipt of disposed lids 16.

Figure 20:
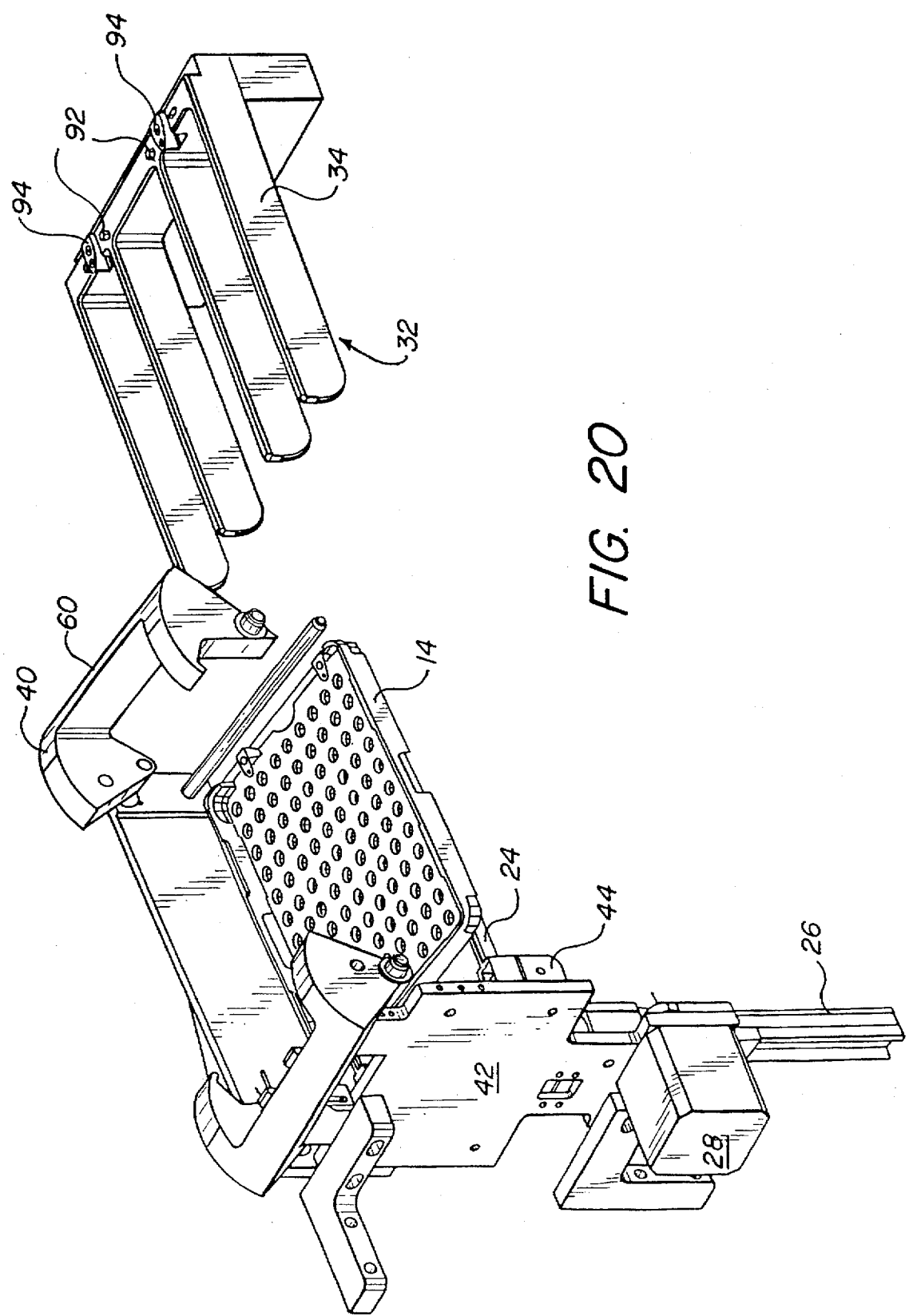
FIG. 20 illustrates the relative positions of the loading mechanism elements of FIG. 1 in unloading an empty tray.

Once the probe tips 12 originally disposed in the tray 10 have been consumed and the tray base portion 10 emptied, the latter must be disposed of prior to loading a fresh tray 10. With reference to FIG. 20, the shaft 26 is elevated to horizontally extend the parallel arms 24 by interference of the cams 44 with the first plate 42. Rather than positioning the arms 42 at the elevation used for transferral of the tray base portion 14 to the delivery rack, wherein the leaf spring latch 48 is positioned to grasp the lid portion 16, the arms 42 are raised to an elevation slightly below this position, wherein the leaf spring latch 42 engages a cooperating aperture on the tray base portion 14 when advanced by the delivery rack 32. Once grasped by the leaf spring latch 42, the delivery rack 32 backs away a short distance, disengaging the base portion 14 from the delivery rack clips 94.

The parallel arms 24 are next raised to support the tray base portion 14 on the parallel arms 24. While this action disengages the base portion 14 from the leaf spring latch 42, the base portion 14 is now resting on the parallel arms 24 above the delivery rack fingers 34, and thus is unaffected by the complete horizontal withdrawal of the delivery rack 32.

With the delivery rack 32 out from under the parallel arms 24, the shaft 26 is lowered by the motor 28, disengaging the cams 44 from contact with the first plate 42 and allowing the parallel arms 24 to swing down to dump the base portion 14. Once again, a disposal chute or receptacle is placed beneath the illustrated mechanism 20 in one embodiment. The mechanism is then ready to repeat the foregoing loading cycle.

Having described preferred embodiments of the invention, it will now become apparent to one skilled in the art that other embodiments incorporating the concepts may be used.

Items other than disposable probe tips may be provided in the trays. Further, the number of items disposed in the trays is determined by the needs of the system to which the present mechanism interfaces. Alternatively, the present invention may be employed in transferring stackable elements such as empty trays or other flat objects, provided the parts to be transferred are vertically spaced apart to enable proper function of the tray guides 40.

The delivery rack 32 is disposed on a horizontal track in one embodiment, and is driven along this track by a motor under control of the control unit 18. Alternatively, the delivery rack 32 is positioned by an actuator having a range of motion sufficient to place the rack 32 under the chute 22 and also away from the chute 22 to an unloading position proximate the analyzer system 30.

In another embodiment of the present invention, the shaft 26 is elevated and lowered by a pneumatic or hydraulic actuator.

In FIG. 1, the loading mechanism 20 is described as providing probe tips to an automated analyzer system 30. However, while the present invention finds utility in transferring piece parts other than probe tips, it also finds utility in providing parts to a system other than an automated analyzer system.

The presently disclosed mechanism 20 can include a reflective sensor or sensors disposed within the chute 22 for determining if at least one tray 10 is properly installed within the chute 22, and if so, if the packaging band 17 has been removed from a pack of three trays 10 installed therein. Yet another sensor may be disposed in the disposal chute or receptacle to detect blockage or fullness. Outputs from these sensors can be provided to the control unit 18 for regulating the operation of the presently claimed invention.

These and other examples of the invention illustrated above are intended by way of example and the actual scope of the invention is to be determined from the following claims.

What is claimed is:

1. A loading mechanism for receiving a quantity of disposable elements in plural vertically spaced sets and for dispensing each set to an element utilization station, said mechanism comprising:

a chute having an open top for retaining a plurality of sets of disposable elements;

a retaining mechanism for holding a lowermost set of disposable elements;

a conveying mechanism having movable arms for cooperatively supporting the lowermost set as said retaining mechanism releases said lowermost set and for lowering the released set while the retaining mechanism catches and holds the next lowermost set; and a pivoting element disposed proximate said retaining mechanism, said pivoting element preventing retraction of said retaining mechanism until being released by interference with said conveying mechanism.

2. The loading mechanism according to claim 1, further comprising a delivery mechanism having a plurality of parallel, horizontally disposed fingers, said delivery mechanism horizontally translatable beneath said chute and intermeshing with said movable arms for receipt and transport of said released set of disposable elements.

3. The loading mechanism according to claim 2, wherein said chute is adpated to retain each set of disposable elements as a horizontal tray supporting a plurality of vertically oriented probe tips, each of said horizontal trays comprising a tray body through which said plurality of vertically oriented probe tips is disposed, and a tray cover adapted for one-dimensional horizontal motion with respect to said tray body.

4. The loading mechanism according to claim 3, said delivery mechanism further comprising at least one clip for releasably engaging said tray body of said released, lowermost set of disposable elements.

5. The loading mechanism according to claim 1, wherein said chute is adpated to retain each set of disposable elements as a horizontal tray supporting a plurality of vertically oriented probe tips.

6. The loading mechanism according to claim 5, wherein said chute is further adpated to retain each of said trays as a tray body through which said plurality of vertically oriented probe tips is disposed, and a tray cover adapted for one-dimensional horizontal motion with respect to said tray body.

7. The loading mechanism according to claim 1, wherein said conveying mechanism further comprises a vertically translating shaft forming a rack elevated by a motor driven pinion.

8. The loading mechanism according to claim 7, further comprising an optical source and detector disposed proximate said shaft, said shaft further comprising notches through which said source conveys light to said detector, said detector providing positional feedback to said motor with regard to said shaft.

9. The loading mechanism according to claim 7, wherein said motor is a stepper motor.

10. The loading mechanism according to claim 1, wherein said chute is adapted to retain said plurality of sets of disposable elements as a plurality of horizontal trays each supporting a plurality of vertically oriented probe tips.

11. The loading mechanism according to claim 1, wherein said movable arms are downwardly aligned in an unload position distal from said chute, and are urged into a horizontal load position by interaction with a portion of said chute.

12. A loading mechanism for receiving a plurality of horizontal probe tip trays and for singly dispensing each of said trays, said mechanism comprising:

a chute having an open top for retaining said plurality of trays in vertical alignment;

two pairs of retractable guides for retaining said plurality of trays and for selectably releasing a lowermost one of said trays through said chute;

a vertically translatable shaft disposed beneath said chute, said shaft having a rack formed thereon;

a pair of movable arms disposed atop said shaft for vertically conveying said released tray beneath said chute; and a pivoting element disposed proximate one of said two pairs of retractable guides, said pivoting element preventing retraction of said retractable guides until said pivoting element is released by interference with said shaft.

13. The loading mechanism according to claim 12, wherein said chute is adapted to retain each of said trays as:

a tray body through which a plurality of vertically oriented probe tips is disposed; and a tray cover adapted for one-dimensional horizontal motion with respect to said tray body.

14. The loading mechanism according to claim 13, further comprising a delivery rack having a plurality of parallel, horizontally disposed fingers, said delivery rack horizontally translatable beneath said chute and intermeshing with said pair of movable arms for receipt and transport of said released tray.

15. The loading mechanism according to claim 14, wherein said delivery rack further comprises at least one clip for releasably engaging a tray body of said released tray.

16. The loading mechanism according to claim 13, wherein said shaft further comprises a leaf spring for engagement with a tray cover of said lowermost tray when said movable arms are proximate said chute, prior to release of said lowermost tray by said retractable guides.

17. The loading mechanism according to claim 12, wherein said movable arms are downwardly aligned in an unload position distal from said chute, and are urged into a horizontal load position by interference with a portion of said chute.

18. The loading mechanism according to claim 17, wherein said shaft is vertically conveyed by interaction of a motor driven pinion with said rack.

19. The loading mechanism according to claim 17, further comprising an optical source and detector disposed proximate said shaft, said shaft further comprising notches through which said source conveys light to said detector, said detector providing positional feedback to said motor with regard to said shaft.

20. The loading mechanism according to claim 12, wherein said retractable guides are retracted by interference with said shaft as said movable arms approach said chute.

21. The loading mechanism according to claim 12, wherein said retractable guides are extended by interference with said shaft as said movable arms descend away from said chute.

22. A loading mechanism for receiving a plurality of horizontal probe tip trays and for singly dispensing each of said trays, said mechanism comprising:

a chute having an open top for retaining said plurality of trays in vertical alignment;

two pairs of retractable guides for retaining said plurality of trays and for selectably releasing a lowermost one of said trays through said chute;

a vertically translatable shaft disposed beneath said chute, said shaft having a rack formed thereon; and a pair of movable arms disposed atop said shaft for vertically conveying said released tray beneath said chute, wherein said retractable guides are extended by interference with said shaft as said movable arms descend away from said chute.

23. A method for providing a tray of probe tips to a utilization station from a loading mechanism, said tray including a base and a lid, said method comprising:

inserting said tray within a chute of said mechanism;

rotating and elevating parallel arms disposed on a shaft from a vertical position to a horizontal position directly beneath said tray using said shaft as a rack and a motor cog as a pinion;

engaging said lid of said tray with a latch adjacent said parallel arms;

releasing said tray onto said parallel arms;

engaging said base of said tray with a clip disposed on a horizontally translating delivery rack;

translating said tray base to said utilization station; and unloading said lid remaining on said parallel arms by lowering said arms whereby said arms rotate to said vertical position and said lid slides off.

24. The method according to claim 23, further comprising the steps of:

translating an empty base on said delivery rack from said utilization station to a position beneath said chute;

engaging said empty base with said latch adjacent said parallel arms;

translating said delivery rack away from said parallel arms, thereby disengaging said empty base from said delivery rack clip;

elevating said empty tray on said parallel arms to unweight said delivery rack;

further translating said delivery rack away from said parallel arms; and unloading said empty base by lowering said arms whereby said arms rotate to said vertical position and said empty base slides off.

25. A loading mechanism for receiving a plurality of horizontal probe tip trays and for singly dispensing each of said trays, said mechanism comprising:

a chute having an open top for retaining said plurality of trays in vertical alignment;

two pairs of retractable guides for retaining said plurality of trays and for selectably releasing a lowermost one of said trays through said chute;

a vertically translatable shaft disposed beneath said chute, said shaft having a rack formed thereon; and a pair of movable arms disposed atop said shaft for vertically conveying said released tray beneath said chute, wherein said retractable guides are retracted by interference with said shaft as said movable arms approach said chute.

26. A loading mechanism for receiving a quantity of disposable elements in plural vertically spaced sets and for dispensing each set to an element utilization station, said mechanism comprising:

a chute having an open top for retaining a plurality of sets of disposable elements;

a retaining mechanism for holding a lowermost set of disposable elements;

a conveying mechanism having movable arms for cooperatively supporting the lowermost set as said retaining mechanism releases said lowermost set and for lowering the released set while the retaining mechanism catches and holds the next lowermost set;

a vertically translating shaft forming a rack elevated by a motor driven pinion; and an optical source and detector disposed proximate said shaft, said shaft further comprising notches through which said source conveys light to said detector, said detector providing positional feedback to said motor with regard to said shaft.

27. A loading mechanism for receiving a plurality of horizontal probe tip trays and for singly dispensing each of said trays, said mechanism comprising:

a chute having an open top for retaining said plurality of trays in vertical alignment;

two pairs of retractable guides for retaining said plurality of trays and for selectably releasing a lowermost one of said trays through said chute;

a vertically translatable shaft disposed beneath said chute, said shaft having a rack formed thereon;

a pair of movable arms disposed atop said shaft for vertically conveying said released tray beneath said chute, said movable arms downwardly aligned in an unload position distal from said chute and urged into a horizontal load position by interference with a portion of said chute; and an optical source and detector disposed proximate said shaft, wherein said shaft further comprises notches through which said source conveys light to said detector, said detector providing positional feedback to said motor with regard to said shaft.

* * * * *